US005665595A

United States Patent [19]

Petell et al.

[11] Patent Number: 5,665,595
[45] Date of Patent: Sep. 9, 1997

[54] IMMUNOGLOBULINS AGAINST INSECT TISSUE

[75] Inventors: James K. Petell, Bay City; Kathi J. Halvin, Saginaw, both of Mich.

[73] Assignee: DowElanco, Indianapolis, Ind.

[21] Appl. No.: 216,119

[22] Filed: Mar. 18, 1994

Related U.S. Application Data

[63] Continuation of Ser. No. 31,072, Mar. 11, 1993, abandoned, which is a continuation of Ser. No. 712,025, Jun. 7, 1991, abandoned.

[51] Int. Cl.⁶ .................. C12N 5/12; C07K 16/44
[52] U.S. Cl. .............. 435/332; 530/388.1; 530/389.1; 530/388.2; 530/389.2
[58] Field of Search .................. 514/2; 530/388.23, 530/389.2, 388.1, 389.1, 388.2; 435/172.2, 70.21, 240.27

[56] References Cited

FOREIGN PATENT DOCUMENTS 9106320  5/1991  WIPO ................ A61K 39/395

OTHER PUBLICATIONS

Terra et al. (1988), Archives of Insect Biochemistry and Physiology, 9:283–297.
Cioff and Wolfersberger (1983), Tissue & Cell 15(5):781–803.
Schlein et al. (1976), Ann. Trop. Med. Parasitol., 70:227.
Schlein et al. (1976), Physiol. Entomol., 1:55, Page 55 only.
Nogge and Giannetti (1980), Science, 209:1028–1029).
Petell et al. (1987) J. Biol. Chem., 262:14753–14759.
Aronson and Touster (1978), Methods Enzymol., 31:90–102).
Hiatt et al., (1989), Nature, 342:76–78.
Lenz et al Arch. Insect Biochem 16:201–212 1991.
Wand Aust J. Biol Sci 28:1–23 1975.
Brosis Abstract Azuma M. et. al.

Primary Examiner—Frank C. Eisenschenk
Attorney, Agent, or Firm—Donald R. Stuart; Andrea T. Borucki

[57] ABSTRACT

The present invention provides a composition and method of protecting plants otherwise susceptible to infestation by insects of the orders Lepidoptera and Coleoptera.

10 Claims, No Drawings

IMMUNOGLOBULINS AGAINST INSECT TISSUE

CROSS-REFERENCE TO RELATED APPLICATION

This is a continuation of application Ser. No. 08/031,072 filed Mar. 11, 1993, now abandoned, which is a continuation of application Ser. No. 07/712,025, filed Jun. 7, 1991, now abandoned.

FIELD OF THE INVENTION

The present invention relates to the fields of immunology, genetic engineering and plant husbandry.

BACKGROUND OF THE INVENTION

Nearly half of the species of insect feed on plants and these maybe further subdivided into those feeding on green plants (phytophagous) and those feeding on fungi (mycetophagous). Predominantly phytophagous groups of phytophagous insects are: Orthoptera, Lepidoptera, Homoptera, Thysanoptera, Phasmida, Isoptera, Coleoptera.

Primary target pests on monocots (e.g., Cereals, Vegetables and Tubers, Oil Crops, Sugar Crops, Forage and Turf Grasses, Fiber Plants and Woods and Spices and Flavorings) are phytophagous beetles or moths of the orders Coleoptera and Lepidoptera.

Primary target pests on dicots (e.g., dicot selected from the group of plant types consisting of Cereals, Protein Crops, Fruit Crops, Vegetables and Tubers, Nuts, Oil Crops, Sugar Crops, Forage Legumes, Fiber Plants and Woods and Spices and Flavorings) are also members of the orders Coleoptera and Lepidoptera.

Lepidopteran insects include, but are not limited to, tomato pinworm (*Keiferia lycopersicella*), tobacco hornworm (*Manduca secta*), (*Trichoplusia ni*), and tomato fruitworm (*Heliothis zea* and *Heliothis virescens*).

Coleoptera insects include, but are not limited to corn rootworm (*Diabrotica* spp., such as *D. longicornis*, *D undecimpunctata* and *D virgifera*) and Colorado potato beetle (*Leptinotarsa* sp., such as *L. decemlineata*).

Many of such insects are relatively specialized feeders. Simply put, pest resistance may be possible because many pests have specialized to a restricted range of host plant. Because of these specializations and because of continued evolutionary pressure exerted by the multitude of plant secondary substances, the physiological/biochemical systems of the alimentary canals in herbivores and pathogens which are vulnerable to plant chemicals are believed to be distinctive in their chemical properties and distinctive in their susceptibility to disruption. Both the pH and proteases in the insect gut lumen have been suggested as important factors (see Jacquet et al. (1987), *Appl. Environ. Microbiol.*, 53:500–504; and Halder et al. (1986), *Eur. J. Biochem*, 156:531–540). Consequently, while insects which feed on the same host plant may be expected to contain enzymes having homologous functions, insufficient information is available regarding alimentary canal membranes to provide an expectation as to the similarity of gut membrane tissue between insects, particularly insects of different orders.

The alimentary canal in insects is divided into three main regions: the foregut (stomodaeum), which is ectodermal in origin; the midgut (mesenteron), which is endodermal, and the hindgut (proctodaeum), which is again ectodermal. In many insects these regions are subdivided into various functional parts, of which the most usual are the pharynx, oesophagus, crop and proventriculus in the foregut, the caeca and ventriculus in the midgut, and pylorus, ileum and rectum in the hindgut.

The midgut in the majority of insects is lined by a delicate peritrophic membrane. The peritrophic membrane of insects eating solid food protects the midgut cells from abrasion; the membrane also acts as a barrier to micro-organisms thus reducing infection of the tissues.

The membrane nearly always contains chitin and protein. The most characteristic midgut cells are tall and columnar with regular microvilli forming a striated border adjacent to the lumen. The basal membranes of the cells, adjacent to the haemocoel, are infolded with few openings to the haemolymph so that the extracellular spaces which they enclose are relatively isolated. The division and differentiation of representative cells occur at crypts in the epithelium, which are visible as small papillae on the outside of the midgut. The circular muscles lie adjacent to the epithelium and are bounded by a delicate connective tissue sheath.

Certain bacterial insecticides act very selectively on different kinds of hosts to effectively disrupt processes in cells or enzymes of the alimentary canal.

The most widely used microbial pesticides are derived from the bacterium *Bacillus thuringiensis* (*B. thuringiensis*). The spore-forming microorganism *Bacillus thuringiensis* produces a crystalline protein toxin. The toxin, upon being ingested in its crystalline form by susceptible insect larvae, is transformed into biologically active moieties by the insect gut juice proteases. The primary target is insect cells of the gut epithelium, which are rapidly destroyed.

For example, certain strains of *B. thuringiensis* produce crystal toxins which are toxic to the larvae of certain lepidopteran insects (see Beegle (1978), *Developments in Industrial Microbiology*, 20:97–104, and U.S. Pat. No. 4,990,332 to Payne, et. al (Mycogen).

Other strains of *B. thuringiensis* produce crystal toxins which are effective against certain species of beetles of the order Coleoptera (see 5,017,373 to Herrnstadt et. al. (Mycogen); and see Krieg et al. (1983), *Z. ang. Ent.*, 96:500–508).

The molecular basis for the differences in insecticidal spectrum of *B. thuringiensis* strains is still incompletely understood. It has been demonstrated that the difference in the insecticidal spectrum of two toxins on the tobacco hornworm (*Manduca sexta*) and the large white butterfly (*Pieris brassicae*) was correlated with the presence of high affinity binding sites on the plasma membrane of gut epithelial cells of target insects (see Van Rie et al. (1990), *Applied and Environmental Microbiology*, 56:1378–1385). Considerable differences in the concentration of binding sites have been observed, reflecting the differences in toxicity (see Hofman et al. (1988), *Proc. Natl. Acad. Sci. USA*, 85:7844–7848).

Clearly it would be advantagous to have a means for a skilled artisan to target a growth inhibitor agaisnt selected species of insects in both the order Lepidoptera and the order Coleoptera. In some instances a skilled artisan may have a growth inhibitor effective against one or a few species within Lepidoptera or Coleoptera. However, it would may also be desired to target a growth inhibitor against species within Lepidoptera and Coleoptera, thus selectively and simultaneously control insects of two major orders of pests.

As described in more detail below, antibodies are protein tetramers having a binding site for specific binding to an antigenic determinant (epitope). Because of their antigenic specificity, antibodies have been used in various insect studies.

Antibodies to muscles or nerves of the flesh fly *Sarcophoga falculata* Pand., when fed to the flies, were found to be attached specifically to the tissue and consequently the metabolism of the flies seemed to be severely disturbed (see Schlein et al. (1976), *Ann. Trop. Med. Parasitol.*, 70:227; and Schlein et al. (1976), *Physiol. Entomol.*, 1:55).

Antiserum containing antibodies directed against albumin, a diet constituent, severely disturbed by feeding such flies (see Nogge and Giannetti (1980), *Science*, 209:1028–1029).

Because of the targeting properties of antibodies and the fact the various flesh eating or blood sucking insects are able to absorb orally administered antibodies. It has been suggested that that it may be possible to use antibodies as an insecticide, providing antigens could be found that gives rise to antibodies that interfere with the metabolism of a target insect.

There are several major concerns associated with the use of antibodies as a selective targeting agent. The antigen against which the antibody is directed must not so unique as to limit the host range to which the antibody may be directed. For example, because of the reported variability of insect alimentary canals, it would not be expected that the midgut epithelium cells of different orders would be suitable targeted antigens. On the other hand, the antigen should not be common so that the antibody is crossreactive to a variety of digestive tissues. For example, it would disadvantageous to have an immunglobulin, particulary if conjugated to a eukaryotic cell inhibitor (e.g., a ribosome inhibiting protein), directed against digestive tissue of insect parasites or predators which normally help control populations of beneficial pests; or directed against digestive tissue of human or other mammal.

To date, no reference has taught the use of a targeting molecule which is capable of recognizing antigenic determinants unique to insects of the orders Lepidoptera and Coleoptera. This lack of a targeting molecule is not surprising because, as previously stated, relatively little is known about invertebrate gut membrane biochemistry—the composition of insect gut membranes in particular have received almost no attention.

Other objects and advantages of the present invention will become apparent from the description of the invention provided hereunder.

SUMMARY OF THE INVENTION

It has been surprisingly discovered that midgut intestinal membrane cells of insects within the orders Lepidoptera and Coleoptera possess cross-reactive antigenic determinants (epitopes). That is, when tested against antigens derived from the intestinal cell membranes from a panel of insect sources, antibodies may be selected which react with insect selectivity, i.e., binding to an antigenic determinant on the midgut intestinal membrane tissue of at least one insect species in the orders Lepidoptera and Coleoptera.

In accordance with a first aspect of the present invention, there has been provided a monoclonal antibody which binds to an antigenic determinant on the midgut intestinal membrane tissue of at least one insect species in the orders Lepidoptera and Coleoptera.

In a second aspect, the present invention provides a composition for application to plants or parts thereof comprising as an active substance an inhibitory amount of a monoclonal antibody which binds to an antigenic determinant on the midgut intestinal membrane tissue of at least one insect species in the orders Lepidoptera and Coleoptera.

In accordance with a third aspect of the present invention, there are provided novel conjugates comprising a monoclonal antibody which binds to an antigenic determinant on the midgut intestinal membrane tissue of at least one insect species in the orders Lepidoptera and Coleoptera and one or more cytotoxins conjugated thereto.

DETAILED DESCRIPTION OF THE INVENTION

The entire teachings of all references cited herein are hereby incorporated by reference.

By "plant" is meant to include seed capable of being germinated into a plant; plant cells; plant protoplasts; plant cell or tissue cultures from which a plant can be regenerated; plant calli; plant clumps; and plant cells that are intact in a plant or parts of a plant, such as flowers, kernels, ears, cobs, leaves, husks, stalks, and the like.

By "antibody" is meant a protein molecule comprising two identical polypeptide chains of about 600 amino acid residues (usually referred to as the heavy chains, H), disulphide bonded to each other, and two identical shorter polypeptide chains of about 220 amino acid residues (usually referred to as the light chains, L), each light chain being disulphide bonded to one end of each heavy chain. The term "antibody" is also intended to include immunologically-active fragments of the above described tetramer.

When the antibody is correctly folded, each chain is formed into a number of distinct globular areas, usually known as domains, joined by a more linear polypeptide chain. The light chains have two such domains, one of which is of variable sequence ($V_L$), and the other of which is of constant sequence ($C_L$). The heavy chains have a single variable domain ($V_H$) adjacent the $V_L$, and three or four constant domains ($C_H$).

The variable domains on both the heavy and the light chains each contain three hypervariable regions which, when the antibody is correctly folded, are located adjacent one another and form the antigen binding site, which recognizes and binds to the antigenic determinant for which the antibody is specific. The constant domains of the antibody do not take part in the binding to the antigenic determinant.

The structure of the antibody and the location of genes coding for various domains thereof are discussed more fully by Early and Hood, In: *Genetic Engineering, Principles and Methods,* (eds) Setlow and Hollaender, 3:153–158.

By "insect selective" is meant antibodies which are specific in the sense that they preferentially bind to selected membrane cells of Lepidoptera and/or Coleoptera, permitting characterization and comparison thereof. By using general screening techniques, a skilled artisan may readily identify and isolate monoclonal antibodies capable of binding to midgut intestinal membrane cells of selected insect species in the orders Lepidoptera and Coleoptera.

By "immunoinhibitor" is meant a polypeptide comprising an antibody having specificity against epitopes of midgut intestinal membrane cells of the orders Lepidoptera and Coleoptera.

By "toxin" is meant to include substances having the property of inhibiting protein synthesis in eukaryotic cells.

By "inhibitory amount" is meant a lethal (toxic) or sublethal (injuring or repelling) amount of an immunoinhibitor.

In a specific embodiment of the present invention, antibodies are raised and selected against an antigenic determinant on the midgut intestinal membrane tissue of at least one insect species in the orders Lepidoptera and Coleoptera.

While not intended to be bound by theory, it is believed that monoclonal antibodies generated against the midgut cells may specifically recognize critical functional sites on proteins or glycoproteins of midgut intestinal membrane tissue required for nutrient digestion and/or uptake or required midgut cellular functions. Antigens include plasma membrane proteins that are apical, lateral and/or basal oriented.

Apical membrane proteins include peptidases (e.g., leucine aminopeptidase, dipeptidyl peptidase IV, aminopeptidase A, enteropeptidases, γ-glutamyl-transferase, and endopeptidases); saccharidases (e.g., sucrase-isomaltase, amylase, trehalase, hydrolases and maltase glucoamylase); and other apical associated proteins (e.g., alkaline phosphatase, guanylate cyclase, various common, transport proteins and insect specific ATPases, cell adhesion molecules, and nutrient receptors). Lateral and basal membrane proteins include alkaline phosphatase, adenyl cyclase, various transferases and various ATPases. Other plasma membrane proteins include various structural membrane components.

In accordance with the present invention, there is provided an immunogenic material for raising antibodies against selected insect species in the orders Lepidoptera and Coleoptera, which material consists essentially of proteins or glycoproteins material derived from midgut intestinal membrane.

Suitable antigens are purified by any technique known in the art. The preparation of suitable antigens first involves the separation of midgut intestinal membrane proteins from outer membrane materials and other nonspecific tissue.

For example, it is known to isolate enriched plasma membrane fractions from isolated midguts and hind-midgut tissue from larvae and insects using density gradient centrifugation or ultrasound (see Terra et al. (1988), Archives of Insect Biochemistry and Physiology, 9:283–297; and Cioff and Wolfersberger (1983), Tissue & Cell 15(5):781–803.

Plasma membrane vesicles from the plasma mebrane of intact insect larvae also may be isolated by mechanical lysing of the cells and separating of outer membrane fractions by sucrose gradient. Alternately, separation of outer membranes may be done by extraction of whole cells with sodium N-lauroyl sarcosinate followed by pelletizing outer membranes by ultracentrifugation (see Petell et al. (1987) J. Biol. Chem., 262:14753–14759, and Aronson and Touster (1978), Methods Enzymol., 31:90–102).

The purified proteins then may be used to stimulate animals for in vivo antibody production. Exemplary host animals include mice, rats, rabbits, and goats.

Immunization protocols are well known and can vary considerably yet remain effective (see Kohler and Milstein (1976), Eur. J. Immunol., 6:511–519; and Schulman et al. (1978), Nature, 276:269–270). Typically, about 1 micrograms (µg) to about 50 µg are given in emulsions of about 1 milliter (ml) to about 2 ml for a rat and one tenth as much for mice.

The first injection of antigen into a host animal may be subcutaneous, intramuscular, intraperitoneal or intravascular. Thereafter, 1 to 10 or more booster immunizations may be given at intervals of between about 2 and about 8 weeks. The route of each immunization may vary according to the protocol used.

After immunization, immune lymphocytes from the immunized animal are fused to myeloma cells to generate hybridoma cell lines which may be cultured indefinitely to produce monoclonal antibodies. The lymphocytes are generally taken either from lymph node tissue or spleen tissue. Specialized myeloma cells, plasmacytomas, have been developed from lymphocyte tumors for use in hybridoma-producing fusion procedures.

In a typical fusion, a suspension of lymphocyte cells is added to the myeloma cells in the presence of a fusogen, most commonly polyethylene glycol (PEG). However, other methods of immortalization are possible, for example, transformation with an immortalizing virus such as the Epstein-Barr virus.

After fusion, the cells are centrifuged and harvested. Thereafter, the cells are diluted and cultured for a week or more in separate wells containing an appropriate selective medium (e.g., HAT medium) that will inhibit the viability of non-fused fusion partners.

After a suitable period of time, culture supernatants from wells demonstrating hybridoma growth are screened to determine the selectivity and range of a given antibody by testing it against panels of isolated (1) midgut intestinal cells from Coleoptera and Lepidoptera and (2) mammalian or other nonspecific tissue. The wells may be screened for the presence of antibody capable of recognizing selected antigenic determinants by any of a number of well-known procedures, such as solid-phase radioimmunoassay, bioassay, enzyme-linked immunosorbent assays, rosetting assays, and blocking assays.

Thereafter, cells from positive wells are plated out into individual cell colonies by limiting dilution. As necessary, feeder cells (e.g., thymocytes or peritoneal exudate cells from an appropriate source) may be added.

After the subcloned hybridomas have grown, as described above, the supernatants may be rescreened for selectivity, as described above. The cloned antibody-producing cells may then be expanded in vitro or in vivo using known procedures.

Antibodies may be categorized by class or subclass, depending on which of a number of possible heavy chain constant domains they contain. Heavy chains are classified according to their constant region: IgA, IgD, IgE IgG, or IgM, with some subclasses among them. Light chains are classified as either kappa (κ) or lambda (λ).

Any suitable technique may be used in the production of the antibodies. Such techniques are known to skilled artisans and include in vitro as well as in vivo techniques.

The amino acid sequence of purified antibody may be determined by automatic Edman degradation using, for example, a Model 470A Protein Sequencer available from Applied Biosystems, Foster City, Calif. Knowledge of the amino acid sequence will permit engineering of desired antibodies.

It is possible to synthesize in vitro an antibody from constituent amino acids. Suitable techniques are the solid phase method for synthesizing sequences of amino acids (see Merrifield (1963), J. Amer. Chem. Soc., 85:2149–2154; and Solid Phase Peptide Synthesis (1969), (eds.) Stewart and Young).

The antibodies also may be prepared in vitro from chromosomal DNA, cDNA or synthetic origin by using well-known techniques.

Cells or other source material containing DNA or RNA coding for the desired antibody may be isolated. In some instances, it may be desirable to isolate the genomic DNA or mRNA (to generate cDNA) from such source material (see Goldfein et al. (1987), *The Journal of Immunology*, 138:940–944). Particularly when significant levels of polynucleotides are not easily obtained, it may be useful to exponentially increase the amount of DNA or mRNA in vitro using sequence specified oligonucleotides via polymerase chain reaction (PCR) (see Mullis et al. (1987), *Meth. Enz.*, 155:335–350; and *PCR Technology*, Erlich (ed.) (1989); and Orlandi et al. (1989), *Proc. Natl. Acad. Sci., U.S.A.*, 86:3387–3837).

An alternative method of obtaining a genetic sequence which is capable of encoding the antibody is by oligonucleotide synthesis. The genetic code is used to determine an oligonucleotide sequence which is capable of encoding the amino acid sequence. In a preferred embodiment, this oligonucleotide sequence is predicted using the codon frequency appropriate for the organism in which the gene is to be expressed. In some cases, alternative codons may be selected to facilitate synthesis and/or provide convenient restriction sites. Translational stop and start signals are added at the appropriate points and sequences to create convenient cloning sites are added to the ends.

A series of oligonucleotides ranging from 20 to 50 bases is synthesized in order to provide a series of overlapping fragments. The oligonucleotides may be chemically synthesized by manual procedures, e.g., the phosphotriester and phosphodiester methods (see Caruthers (1983), In: *Methodology of DNA and RNA*, (ed.) Weissman); or automated methods e.g., using diethylphosphoramidites as starting materials (see Beaucage et al.(1981), *Tetrahedron Letters*, 22:1859–1962). The synthesized oligonucleotides are then when annealed and ligated to produce both strands of the gene (see Ausebel, et al, *Current Protocols in Molecular Biology* (1989) and Sambrook et al. (1989), *Molecular Cloning: A Laboratory Manual*).

The polynucleotides and peptides thus prepared may be isolated and purified by procedures well known in the art. Exemplary techniques may be used for the purification, such as electrophoresis, sucrose or cesium chloride gradient fractionation, adsorption to a specific binding column or combinations thereof (see *Current Protocols in Molecular Biology* (1989), supra; and *Molecular Cloning: A Laboratory Manual* (1989), supra).

It should be understood that one may engineer an antibody heavy chain or light chain variable region effectively homologous to the antibody heavy chain or light chain variable region of a desired known antibody. "Effectively homologous" refers to the concept that the primary amino acid sequence of the variable region may be altered but that the antibody retains a binding site with the capacity to bind to the same antigen or epitope. Accordingly, such variations and derivations are considered to be within the scope of the present invention.

This may be demonstrated by experiments which show crossblocking of an exemplified monoclonal antibody by the effectively homologous monoclonal antibody. Crossblocking occurs as a result of one antibody binding to the same epitope as a second antibody, or as a result of an antibody binding to a second epitope which is so closely situated on the same antigen that binding of one antibody to the first epitope blocks the binding of a second antibody to the second epitope.

Modifications contemplated by the present invention include the addition, deletion, or nonconservative substitution of a limited number of various amino acids. Generally, an amino acid sequence is effectively homologous to a second amino acid sequence if at least 70 percent, preferably at least 80 percent, and most preferably at least 90 percent of the active portions of the amino acid sequence are homologous. General categories of potentially-equivalent amino acids are set forth below, wherein amino acids within a group may be substituted for other amino acids in that group: (1) glutamic acid and aspartic acid; (2) hydrophobic amino acids such as valine, leucine and isoleucine; (3) asparagine and glutamine; (4) threonine and serine; (5) glycine and alanine; (6) phenylalanine, tyrosine, and tryptophan; and (7) lysine and arginine. Accordingly, such variations and derivations are considered to be within the scope of the present invention.

Fragments of antibodies include segments of proteolytically-cleaved or recombinantly-prepared portions of an antibody. Thus, for example, the variable and constant domains of the antibody may be specifically altered, or partially or completely omitted. Nonlimiting examples of such recombinant fragments include "Fab", "F(ab')$_2$", and "Fab'". Additionally, the antibody may be modified to an "Fv" (see U.S. Pat. No. 4,642,334 to Moore (DNAX)). Still further, the antibody may be modified to form single chain $F_v$ molecules (see U.S. Pat. No. 4,496,778. Further, the CDR of an antibody may be synthesized and the polypeptide used to bind to a selected antigen (see Williams et al. (1989), *Proc. Natl. Acad. Sci., USA*, 86:5537–5541).

It should be understood that the genetic sequence used to encode the protein may vary with the particular antibody, with expression of the protein, and may vary the level of toxicity toward the selected insects. Generally, antibody fragments may be more easily expressed and, therefore, are preferred. Moreover, antibodies of smaller molecular weight are more likely to be capable of traversing the peritropic membrane. As a general consideration whole pentameric IgM antibodies may not be most efficacious, from a molecular weight perspective; however, other considerations may warrant use of such antibodies.

Exemplary techniques for modifying olionucleotide sequences encoding the antibody light or heavy chains include polynucleotide-mediated, site-directed mutagenesis, i.e., using a single strand as a template for extension of the oligonucleotide to produce a strand containing the mutation, (see Zoller et al. (1984), *DNA*, 3:479–488); and PCR, i.e., using sequence specified oligonucleotides (see Higuchi et al. (1988), *Nucl. Acids Res.*, 16:7351–7367, Ho et al. (1989), *Gene*, 77:51–59, and Horton et al. (1989), *Gene*, 77:61; and *PCR Technology: Principles and Applications for DNA Amplification*, (ed.) Erlich (1989)).

The above discussed methods may be used to prepare genetic sequences which are capable of encoding the antibody light or heavy chains. In order to further characterize such genetic sequences, it is desirable to express the proteins which these sequences encode, and confirm that they possess desired binding characteristics of antibody.

By appropriate choice of restriction sites, a desired DNA fragment may be positioned in a biologically functional vector preferably containing appropriate control sequences not present in the selected DNA fragment. By "biologically functional" is meant that the vector provides for replication and/or expression in an appropriate host, either by maintenance as an extrachromosomal element or by integration into the host genome.

A vector should contain all the DNA sequences necessary for both replication and expression of a heterologous DNA sequence in a given host. Expression of a heterologous DNA coding sequence has been shown to require the following components: a promoter sequence, a transcriptional start or leader sequence (e.g. 5' non-translated region found in messenger RNA) which is typically contained adjacent to and within the promoter sequence, a DNA sequence coding for translation start-signal codon, a DNA sequence coding for the desired (e.g. heterologous) polypeptide product, at least one DNA triplet coding for a translation terminator codon, and a DNA sequence coding for a 3' non-translated region containing a polyadenylation signal. Finally, the vector should desirably have a marker gene that is capable of providing a phenotypical property which allows for identification of host cells containing the vector.

Where stable episomal maintenance or integration is desired, a vector will be employed which has a replication system which is functional in the host. The replication system may be derived from the chromosome, an episomal element normally present in the host or a different host, or a replication system from a virus which is stable in the host.

DNA fragments coding for the light chain and heavy chain may be inserted into separate vectors, or into the same vector. Techniques for such manipulations are well known in the art (see Ausebel, et al, (1989), supra and Sambrook et al. (1989), supra).

A large number of vectors are available or can be readily prepared for viruses, prokaryotic or eukaryotic cells, and are well known to skilled artisans. In general, vectors suitable for prokaryotic microbes may be used (e.g., Col E1, pcR1, pBR322, pACYC 184 and RP4, λ phage DNA or derivatives of any of these). Suitable vectors for eukaryotic microbes include plasmids based on a 2 micron origin. Any vector containing an appropriate gene promoter sequence may be used for cloning in higher eukaryotic systems, e.g. pSV2neo.

Restriction endonucleases may be used as a means for inserting the DNA fragments encoding the antibody into an appropriate vector. Exemplary restriction enzymes include Aat II, Bam HI, Eco RI, Hind III, Nde I, Spe I, Xba I, Sac I, Bgl II, Pst I, Sal I and Pvu II.

Cleavage is performed by treating the vector with a restriction enzyme(s). In general, 10 μg vector or DNA fragments is used with 10 units of enzyme in 100 μl of buffer solution. Endonuclease digestion will normally be carried out at temperatures ranging from 37° C. to 65° C., at a pH of 7 to 9. Appropriate buffers and substrate amounts for particular restriction enzymes are specified by the manufacturer. Time for the reaction will vary between from 1 to 18 hours.

After the restriction enzyme digestion is complete, protein may be removed by standard techniques (e.g., extraction with phenol and chloroform). The nucleic acid may be then recovered from the aqueous fraction by standard techniques.

The desired fragment then may be purified from the digest. Suitable purification techniques include gel electrophoresis or sucrose gradient centrifugation. The vector and foreign DNA fragments may then be ligated with DNA ligase.

An appropriately buffered medium containing the DNA fragments, DNA ligase, and appropriate cofactors may be employed. The temperature employed will be between 4° C. to 25° C. When DNA segments hydrogen bond, the DNA ligase will be able to introduce a covalent bond between the two segments. The time employed for the annealing will vary with the temperature employed, the nature of the salt solution, as well as the nature of the sticky ends or cohesive termini. Generally, the time for ligation may be from 5 to 18 hours (see. Ausebel, et al, (1989), supra and Sambrook et al. (1989), supra).

Exemplary host cells include unicellellar include prokaryotic and eukaryotic strains. Prokaryotic microbes that may be used as hosts include *Escherichia coli.*, Bacilli, and other enterobacteriaceae such as *Salmonella typhimurium*, and various Pseudomonas. Common eukaryotic microbes include *S. cerevisiae* and *Pichia pastoris*.

Common higher eukaryotic host cells include Sp2/0 or CHO. Another preferred host is insect cells, for example Drosophila larvae, in which the vector contains the Drosophila alcohol dehydrogenase promoter. Alternatively, baculovirus vectors. e.g., *Autographa californica* nuclear polyhedrosis virus (see Miller et al. (1983), *Science*, 219:715–721) may be engineered to express large amounts of the antibody in cultured insects cells.

Finally, cells from and portions of higher plants have been found useful as recombinant hosts, and appropriate control sequences are available for expression in these systems. Suitable plant cells include cells derived from, or seedlings of, tobacco, petunia, tomato, potato, rice, maize and the like.

Promoters which are known or are found to cause production of a mRNA transcript in plant cells may be used in the present invention. Suitable promoters may include both those which are derived from a gene which is naturally expressed in plants and synthetic promoter sequences which may include redundant or heterologous enhancer sequences.

A number of promoters which are active in plant cells include the nopaline synthase, octopine synthase and mannopine synthase promoters which are carried on tumor-inducing plasmids of *Agrobacterium tumefaciens*, the cauliflower mosaic virus 19S and 35S promoters, and the light-inducible promoter from the small subunit of ribulose bis-phosphate carboxylase. These types of promoters have been used to create various types of DNA constructs expressed in plants (see PCT publication WO 84/02913 to Rogers et al. (Monsanto)).

Examples of other suitable 3' regions are the 3' transcribed, non-translated regions containing the polyadenylation signal of the nopaline synthase gene of the Agrobacterium tumor-inducing plasmid or the conglycinin storage protein gene.

Suitable vectors for transforming plant tissue and protoplasts have been described in the literature (see deFrammond et al. (1983), *Biotechnology*, 1:262; An et al. (1985), *EMBO J.* 4:277; Potrykus et al. (1985), *Mol. Gen. Genet.* 199:183; Rothstein et al. (1987), *Gene*, 53:153; and WO 90/08829 to Bridges, et al. (Imperial Chemical Company)).

Thereafter, the vector constructions may be used to transform an appropriate host cell by any suitable method. The host cells may be transformed via either cotransformation or targeted transformation.

For cotransformation, the genes coding for the light chain and heavy chain may be used to transform separate cell cultures, either of the same or of differing species; separate plasmids for light and heavy chain may be used to co-transform a single cell culture; or finally, a single vector containing both genes and capable of expressing the genes for both light and heavy chain may be transformed into a single cell culture.

For targeted transformation, the host cells are transformed with genes encoding for one light chain, and the cells containing the chain marker are selected. The chain is found using cytostaining or possibly by detection in the supernatant if it has been secreted. Cells selected to have the chain are transformed with constructs of the other chain, and resultant cells containing the additionally chain marker selected.

The appropriate procedure may be chosen in accordance with the host cell used. Conventional technologies for introducing biological material into host cells include electroporation (see Shigekawa and Dower (1988), *Biotechniques*, 6:742; Miller, et al. (1988), *Proc. Natl. Acad. Sci. USA*, 85:856–860; and Powell, et al (1988), *Appl. Environ. Microbiol.*, 54:655–660); direct DNA uptake mechanisms (see Mandel and Higa (1972), *J. Mol. Biol.*, 53:159–162; Dityatkin, et al. (1972), *Biochimica et Biophysica Acta*, 281:319–323; Wigler, et al. (1979), *Cell*, 16:77; and Uchimiya, et al. (1982), In: *Proc. 5th Intl. Cong. Plant Tissue and Cell Culture*, A. Fujiwara (ed.), Jap. Assoc. for Plant Tissue Culture, Tokyo, pp. 507–508); fusion mechanisms (see Uchidaz, et al. (1980), In: *Introduction of Macromolecules Into Viable Mammalian Cells*, Baserga et al. (eds.) Wistar Symposium Series, 1:169–185); infectious agents (see Fraley, et al. (1986), *CRC Crit. Rev. Plant Sci.*, 4:1–46); and Anderson (1984), *Science*, 226:401–409); microinjection mechanisms (see Crossway, et al. (1986), *Mol. Gen. Genet.*, 202:179–185); and high velocity projectile mechanisms (see EPO 0 405 696 to Miller, Schuchardt, Skokut and Gould, (The Dow Chemical Company).

Generally, after being transformed, the host cells is grown for about 48 hours to allow for expression of marker genes. The cells are placed in selective and/or screenable media, where untransformed cells are distinguished from transformed cells, either by death or a biochemical property.

It is envisaged that in preferred forms of the invention, the individual chains will be processed by the host cell to form the complete polypeptide or protein which advantageously is secreted therefrom. However, it may be that the individual chains may be produced in insoluble or membrane-bound form. It may therefore be necessary to solubilize the individual chains and allow the chains to refold in solution to form the active antibody.

The transformants are then tested for immunogenic activity. Selected positive cultures are subcloned in order to isolate pure transformed colonies to express substantially pure protein. The colonies can be assayed, for example, by Northern blotting, for the presence of antibody protein mRNA. Alternately, the level of toxin protein may be assayed by immunoassay such as Western blot. Exemplary assay techniques also include enzyme-linked immunosorbent assay, radioimmunoassay, or fluorescence-activated cell sorter analysis, immunohistochemistry and the like.

Uses of the Invention

The antibodies of the present invention may be used to characterization and compare different species in the orders Lepidoptera and Coleoptera on the basis of antigenic determinants on midgut intestinal membrane tissue.

The present invention provides a means to protect plants which are susceptible to infestation by Coleoptera and/or Lepidoptera by application of an immunoinhibitor against selected species of insects in the orders Lepidoptera and Coleoptera.

Thus, the present invention provides a composition and method to selectively and simultaneously control insects of two major orders of pests. While the immunoinhibitor may be an insect growth inhibitor agent in its own right, it is envisaged that the immunoinhibitor may be coupled to one or more insect growth inhibitors to form a molecule directed to midgut cells within specific.

The insect growth inhibitors substances may be selected from a group of growth inhibitor proteins of plant, fungal or bacterial origin.

The following proteins belong to this class of toxins, e.g., gelonin, pokeweed antiviral proteins, dodecandrin, dianthins, luffin, saporins, Momardica charantia inhibitor, grain inhibitors and two-subunit toxins such as ricin, abrin, modeccin, volkensin and viscumin.

The fungal protein toxins, e.g.: α-Sarcin, restrictocin and mitogillin are closely related basic proteins. These toxins contain a single polypeptide chain and unlike most of the plant toxins do not contain a carbohydrate moiety.

Diphtheria toxin and Pseudomonas exotoxin are two examples of bacterial toxins that show functional similarities with the above-described 2 subunit plant toxins.

Examples of enzymatically active toxins and fragments thereof include diphtheria A chain, nonbinding fragments of diphtheria toxin, exotoxin A chain (from *Pseudomonas aeruoinosa*), ricin A chain, abrin A chain, modeccin A chain, alpha-sarcin, *Aleurites fordii* proteins, dianthin proteins, *Phytolacca americana* proteins (PAPI, PAPPII, and PAP-S), momordica charantia inhibitor, curcin, crotin, saponaria officinalis inhibitor, gelonin, mitogellin, restrictocin, phenomycin, maize ribosoime inactivating protein and enomycin.

The antibody and insect growth inhibitor are generally bound by any covalent bond which allows the toxin to travel to the target cell with the antibody. The only criteria is that the bond must be achieved in a manner which does not significantly decrease the binding specificity and avidity of the antibody for its epitope.

For a general discussion of chimeric toxins, see, for example, Pastan and FitzGerald (1989), *The Journal of Biological Chemistry,* 264:15157–15160; and U.S. Pat. No. 4,892,827. For details of antibody conjugates, reference may be made to *Handbook of Experimental Immunology* (1978), (ed.) Weir, Blackwell Scientific, vol. 3.

The present invention provides an agricultural composition for application to plants or parts thereof which is susceptible to infestation by Coleoptera and/or Lepidoptera, said agricultural composition comprising one or more inhibitor. Often the agricultural composition will contain an agriculturally acceptable carrier. By the term "agriculturally acceptable carrier" is meant a substance which may be used to dissolve, disperse or diffuse an active compound in the composition without impairing the effectiveness of the compound and which by itself has no detrimental effect on the soil, equipment, crops or agronomic environment.

Agricultural compositions must be suitable for agricultural use and dispersal in fields. Generally, components of the composition must be non-phytotoxic, nonbacteriostatic and non-bacteriocidal. Foliar applications must not damage or injure plant leaves. In addition to appropriate liquid or solid carriers, compositions may include sticking and adhesive agents, emulsifying and wetting agents. Agricultural compositions for insect pest control may also include agents which stimulate insect feeding.

The agricultural compositions may be applied in a wide variety of forms including powders, crystals, suspensions, emulsified suspensions, dusts, pellets, granules, encapsulations, microencapsulations, aerosols, solutions, gels or other dispersions.

Additional agents may be included as adjuvants, such as wetting agents, spreading agents, dispersing agents, or adhesives, according to conventional agricultural practices. Adjuvants for the formulation of insecticides are well-known to those skilled in the art.

An additional kind of adjuvant includes insecticidal, fungicidal, biocidal, herbicidal and fertilizer compounds and compositions compatible with the immunoinhibitor, capable of expanding the spectrum of target pests, to extend the duration of effectiveness of the antibody or to help stabilize the agricultural composition. Such potentiators would include lectins, amphipathic peptides, amphipathic proteins or proteinase inhibitors.

The concentration of immunoinhibitor will vary widely depending upon the nature of the particular formulation, particularly whether it is a concentrate or it is to be used directly. The immunoinhibitor will be present in at least 1 percent by weight and may be up to 100 percent by weight. The dry formulations will have from about 1 to about 95 percent by weight of the antibody while the liquid formulations will generally be from about 1 to about 60 percent by weight of the solids in the liquid phase.

The presentation of the agricultural composition may be achieved by external application. This application of the agricultural composition may be either directly or in the vicinity of the plants or plant parts. The agricultural compositions may be applied to the environment of the target pest(s), e.g., plants, soil or water, by spraying, dusting, sprinkling, or the like.

The present invention also contemplates the use of a baculovirus containing a gene encoding the immunoinhibitor. Baculoviruses enter the cell by endocytosis and move to the nucleus where their DNA is released. Replication is followed by viral assembly in the nucleus of the infected cell. The baculoviruses are lytic and thus quickly kill their insect host after infection.

The recombinant baculovirus may be formulated into an agricultural composition in a variety of ways. It may be employed in wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The agricultural compositions may include spreader-sticker adjuvants, stabilizing agents, other insecticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

In general, such agricultural compositions may be applied at any time during plant growth. Inoculation of large fields of plant in particular may be accomplished most effectively by spraying.

The present invention further contemplates a microbial host capable of colonizing on or near a selected plant or plant part transformed with a gene encoding the antibody.

Characteristics of particular interest in selecting a host for purposes of production include ease of introducing a genetic sequence encoding a immunoinhibitor, availability of expression systems, efficiency of expression, stability of the insecticide in the host, and the presence of auxiliary genetic capabilities. Characteristics of interest for use as an insecticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the insect growth inhibitor; and the like. Other considerations include ease of formulation and handling, economics, storage stability, and the like.

Preferred microbial hosts are capable of being treated to prolong the activity of the immunoinhibitor when the then microbial host is applied to the environment of target pest(s), suitable microbial hosts are normally limited to those hosts which do not produce substances toxic to higher organisms, such as mammals. However, organisms which produce substances toxic to higher organisms may be used, where the insect growth inhibitor is unstable or the level of application is sufficiently low as to avoid any possibility of toxicity to a mammalian host. A microbial host of particular interest will be the prokaryotes and the lower eukaryotes, such as fungi.

The microbial host selected to act as carrier for delivering an insect growth inhibitory protein to the surface of plants may, in principle, be chosen from a wide range of bacteria that colonize diverse plants but are not pathogenic to plants. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium and Rhizobacter; Spirillaceae (such as photobacterium), Zymomonas, Serratia, Aeromonas, Vibrio, Desulfovibrio, Spirillum; Lactobacillaceae; Pseudomonadaceae (such as Pseudomonas and Acetobacter); Azotobacteraceae and Nitrobacteraceae. Among eukaryotes are fungi (such as Phycomycetes and Ascomycetes), which includes yeast (such as Saccharomyces and Schizosaccharomyces); and Basidiomycetes yeast (such as Rhodotorula, Aureobasidium, Sporobolomyces).

The antibody may be used to enhance the toxicity of insecticidal microbes. Several baculoviruses including those that infect *Heliothis virescens* (cotton bollworm), *Orgyla pseudotsugata* (Douglas fir tussock moth), *Lymantia dispar* (gypsy moth), *Autographica californica* (alfalfa looper), *Neodiprion sertifer* (European pine fly) and *Laspeyresia pomonella* (coddling moth) have been registered and used as pesticides (see U.S. Pat. No. 4,745,051 and EP 175 852).

The host may be formulated in a variety of ways. It may be employed in wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other insecticidal additives surfactants, and bacterial nutrients or other agents to enhance growth or stabilize bacterial cells. Liquid formulations may be aqueous-based or non-aqueous and employed as foams, gels, suspensions, emulsifiable concentrates, or the like. The ingredients may include rheological agents, surfactants, emulsifiers, dispersants, or polymers. The formulations will generally have from about $10^2$ to about $10^4$ cells/mg. These formulations will be administered at about 50 mg (liquid or dry) to about 1 kg or more per hectare.

The host may be applied to the situs of Diabrotica pests where they will exist, and preferably proliferate, and be ingested by the susceptible beetles. In general, inoculants can be applied at any time during plant growth. Inoculation of large fields of plant in particular may be accomplished most effectively by spraying.

The present invention also contemplates the transform other plant tissues with antibody. Exemplary tissues include, but are not limited to, embryos, apical and other meristems, buds, somatic and sexual cells, tissues or organs in vivo and in vitro. The appropriate procedure to transform and produce mature plants may be chosen in accordance with the plant species used (see Hiatt et al., (1989), *Nature*, 342:76–78).

The transformed plant cells may be chimeric with respect to the incorporated foreign DNA. If the cells containing the foreign DNA develop into either micro- or macrospores, the integrated foreign DNA will be transmitted to sexual progeny. If the cells containing the foreign DNA are somatic cells of the plant, non-chimeric transgenic plants are produced by conventional methods of vegetative propagation either in vivo, from buds or stem cuttings, or in vitro following established procedures chosen in accordance with the plant species used.

The present invention also contemplates the use of transformed plant tissues susceptible to infestation by Coleoptera and Lepidoptera pests. Exemplary tissues include, but are not limited to, embryos, apical and other meristems, buds, somatic and sexual cells, tissues or organs in vivo and in vitro. The appropriate procedure to transform and produce mature plants may be chosen in accordance with the plant species used.

The mature plants, grown from the transformed plant cells, are selfed to produced an inbred plant. The inbred plant produces seed containing the gene encoding the antibody. These seeds can be grown to produce plants that have the antibody.

The inbreds according to this invention may be used to develop insect tolerant hybrids. In this method, an insect tolerant inbred line is crossed with another inbred line to produce the hybrid.

Parts obtained from the regenerated plant, as flowers, seeds, leaves, branches, fruit, and the like are covered by the invention provided that these parts comprise the insect tolerant cells. Progeny and variants, and mutants of the regenerated plants are also included within the scope of this invention.

In diploid plants, typically one parent may be transformed and the other parent is the wild type. After crossing the parents, the first generation hybrids ($F_1$) will show a distribution of ½ immunoinhibitor/wild type: ½ immunoinhibitor/wild type. These first generation hybrids ($F_1$) are selfed to produced second generation hybrids ($F_2$). The genetic distribution of the $F_2$ hybrids is ¼ immunoinhibitor/immunoinhibitor: ½ immunoinhibitor/wild type: ¼ wild type/wild type. The $F_2$ hybrids with the genetic makeup of antibodyantibody are chosen.

In addition, it is contemplated that the transformed plant cells and their progeny may be used to control pests by applying to the pests and/or the habitat of said pests (i.e., the locus to be protected, for example, to a growing crop or to an area where a crop is to be grown) an inhibitory amount of transformed plant matter alone or together with other components.

Compositions and formulations are prepared in a known manner. The amount of transformed plant matter to be used depends on a variety of factors, for example, the kind of pest, the formulation or composition used, the state of the crop infected with the pest and the prevailing weather conditions. In general, transformed plant cells and their progeny may constitute from about 0.1 to about 100 percent by weight of the composition or formulation and preferably from about 1.0 to about 99 percent by weight.

EXAMPLES

The present invention is illustrated in further detail by the following examples. The examples are for the purposes of illustration only, and are not to be construed as limiting the scope of the present invention. All parts and percentages are by weight unless otherwise specifically noted.

Method for Isolation of Enriched Plasma Membrane Vesicles from Diabrotica Midgut An isolation scheme was developed to obtain plasma membrane vesicles of midgut epithelial cells from corn rootworm larvae using a modified differential sucrose centrifugation described by Petell et al. (1987), supra and Aronson and Touster (1978), supra.

Diabrotica larvae were homogenized in 3 volumes of cold isotonic sucrose (0.25M sucrose, 5 mM Tris-HCl, pH 8.0) containing proteolytic inhibitors (1 mM phenylmethyl sulfonylfluoride (PMSF), 400 μg/ml (5000 Klu/ml) aprotinin, 125 μg/ml leupeptin, and 250 μg/ml antipain) with a single up-and-down stroke of a Potter-Elvehjem tissue grinder powered by an electric drill (1200 rpm). The homogenate was centrifuged at 1000 rpm for 10 minutes. The supernatant was decanted and saved and the pellet was re-extracted in 3 volumes of extraction and centrifuged as before. The supernatant was added to the first supernatant and the pellet was re-extracted and centrifuged a third time. The combined supernatant fractions referred to as E fractions were centrifuged for 20,500 rpm for 8 minutes. The pellet obtained is referred to as M. The supernatant was centrifuged for 33,000 rpm for 90 minutes. The supernatant of this centrifugation is referred to as S fraction and the pellet as P fraction.

The P fraction was resuspended by two up-and-down strokes of tissue grinder in 2.5 volumes of 57% sucrose (refractory index of 1.4351) in 0.25M sucrose, 5 mM Tris-HCl, pH 8.0, 1 mM PMSF. The final refractory index of the resuspended sample was 1.4010 or greater. Approximately 12 ml of homogenate was placed in polyalomer tube (36 ml total volume), layered with 17 ml of 34% sucrose, 5 mM Tris-HCl, pH 8.0, 1 mM PMSF (refractory index of 1.3884) and topped with 7 ml of 0.25M sucrose, 5 mM Tris-HCl, pH 8.0. The gradients were centrifuged at 25,000 rpm for 16 hours in a swinging bucket rotor without brake. Flocculent material present at the 34%-0.25M sucrose interface was referred to as $P_{21}$ and just above this interface in the 0.25M sucrose as $P_{2u}$. The M fraction was similarly subjected to gradient preparation. Flocculent material at and above the 34%-0.25M sucrose interface was referred to $M_{21}$ and $M_{2u}$. Material was obtained from the 57%–34% interface was denoted $M_3$. All flocculent fractions were resuspended in a large volume of 5 mM Tris-HCl, pH 8.0, 1 mM PMSF and centrifuged for 45,000 rpm for 1 hour. Pelleted fractions were dissolved in a small of 5 mM Tris-HCl, pH 8.0, 1 mM PMSF and proteolytic inhibitors. Fractions were placed in ice and assayed for enzymatic activity and protein concentrations.

Insect larvae subcellular fractions were assayed for marker enzyme activity which included leucine aminopeptidase as a marker of the apical domain of epithelial cells and cytochrome oxidase for mitochondria as described by Roman and Hubbard (1983), *J. Cell Biol.*, 96:1548–1558, and Cooperstein and Lazarow (1951), *J. Biol. Chem.*, 189:655–670. Enzymatic activities were calculated per milligram of protein for each fraction. Specific activity was calculated per milligram of protein for each fraction. Specific activity of each fraction was expressed as an initial E fraction. Leucin aminopeptides activity was highly enriched in the $P_{21}$, $M_{2u}$ and $M_{21}$ fractions while cytochrome oxidase activity was enriched in the $M_3$ fraction.

Preparation of Monoclonal Antibodies (mAb) to Diabrotica Midgut Proteins

Mice (Balb-c) were injected intraperitoneally with 50 μg of sonicated membrane fractions ($P_{2u}$, $P_{21}$ and $M_{2u}$) enriched for leucine aminopeptidase in Freund's complete adjuvant. After initial injection, mice were boosted every two weeks with 25 μg of membrane protein in incomplete Freund's adjuvant for at least 5 weeks prior to fusion. Three to four days prior to hybridoma fusion event, mice were injected intravenous 25 µg of membrane protein.

The mice were sacrificed by cervical dislocation and the spleens removed aseptically. Single cell suspensions of spleen cells were prepared by expelling the cell mass from the spleen sac. Spleen cells were washed twice with RPMI, mixed in a ratio of 4:1 with myeloma cells from the line P3 X63 Ag8.653 in RPMI, and fused in 45% v/v polyethylene glycol (molecular weight 3700). After fusion, cells were plated out at 2×10⁴ cells/well in 96 well plates using RPMI-1640 medium containing mM L-glutamine, mM sodium pyruvate, penicillin and streptomycin.

The medium was supplemented with 10% v/v fetal bovine serum (Hyclone Laboratories, Logan, Utah) and $10^4$ murine peritoneal exudate cells/well. For the selection of hybrids, the medium was further supplemented with HAT (Sigma Chemical Company, St. Louis, Mo.) according to the manufacturer's instructions. The cells were incubated at about 37° C. in 5% $CO_2$.

Primary Screening by ELISA

Antibodies were initially screened for activity against various target insects by measuring the ability of the antibodies to bind to gut membrane proteins. Approximately two weeks after fusion event, HAT-selected hybridoma cells were screened by an enzyme linked immunosorbent assay (ELISA) to detect IgG antibody molecules which bound to Diabrotica midgut membrane proteins.

Initial screening was performed using 5 to 10 µg per well of P/M combined fractions, dried on Immunlon 1™ plates (Dynatech, Chantilly, Va.) overnight in phosphate buffered saline (PBS). Non-specific binding was minimized by incubating the antigen-coated plates with 200 µl/well of 1% bovine serum albumin (BSA) in PBS for 30 minutes at 37° C. After removal of BSA/PBS, about 50 µl of hybridoma media was added to each well and incubated for 60 minutes at 37° C. Plates were washed three times with 0.025% solution of Tween 20. The presence of bound antibodies was detected by addition of goat anti-mouse gamma chain conjugated to alkaline phosphatase in 1% BSA/PBS to each well for 60 minutes at 37° C. Plates were washed three times with 0.025% solution of Tween 20. Colored product generated by alkaline phosphatase reaction with with p-nitrophenyl phosphate indicated the presence of mouse IgG bound to antigen. Media giving an optical density of more than twice background were selected and expanded.

After two weeks, positive hybridomas were rescreened in a goat anti-mouse gamma chain antibody trap, using the ELISA procedure described above. Those media containing twice background were selected for continued expansion and secondary screening by indirect fluorescent immunocytochemistry.

Secondary Screening by Indirect Immunofluorescent of Diabrotica Midgut Frozen Sections Indirect immunofluorescent staining of Diabrotica larval midgut frozen sections was performed as a modification of the protocol described by Petell et al. (1987), supra. Midguts were dissected from insect of interest, immersed in O.C.T. TISSUE TEK™ embedding compound (Miles Labs, Elkhart, Ind.) and immediately frozen in liquid nitrogen. Four to six µm thick sections of insect midgut were cut using a cryostat microtome, placed on glass slides and dried overnight at room temperature. Slides were immersed in a fixing solution of 4% methanol-free formaldehyde in PBS for 1 hour at 4° C. followed by transfer to 100 mM glycine in PBS for 30 minutes at 4° C. and to 0.2% BSA/PBS for 30 minutes at room temperature. For staining, microfuged hybridoma media was added to section and incubated for 30 minutes at room temperature in a humidity chamber. Slides were washed once in 0.2% bovine serum albumin/phosphate buffered saline (BSA/PBS) followed by 2 washes with PBS. Sections were incubated with goat anti-mouse IgG fluorescein conjugated antibody for 30 minutes at room temperature followed by 3 washes in PBS. Slides were dried and mounted in glycerol/PBS, 9:1, and viewed in a microscope with epifluorescence attachment. The results are set forth in Table 1

TABLE 1

Comparative Localization of Monoclonal Antibodies to Insect and Mammalian Gut

| mAb | WSCB | WCR | CPB | TBW/THW | Rat |
|---|---|---|---|---|---|
| P2L 12 | basal lamina | basal lamina | — | — | — |
| P2L 13 | basal lamina | — | — | — | — |
| M2U 62 | basal lamina | — | — | — | — |
| M2U 63 | basal lamina | basal lamina | — | — | — |
| M2U 72 | basal lamina | basal lamina | basal lamina | — | — |
| M2U 79 | basal lamina | basal lamina | basal lamina | — | — |
| M2U 141 | basal lamina | basal lamina | basal lamina | — | basal lamina |
| M2U 146 | basal lamina | basal lamina | basal/apical | basal lamina | — |
| M2U 151 | basal lamina | basal lamina | basal/apical | — | — |
| M2U 85 | basal, apical | basal, apical | basal, apical | basal, apical | crypt/intracell |
| M2U 89 | apical/basal | apical/basal | basal lamina | — | — |
| M2U 96 | apical | apical | — | — | — |
| M2U 100 | apical | apical | — | — | — |
| M2U 110 | apical | apical | basal lamina | — | — |

WSCB western spotted cucumber beetle *Coleoptera:diabortica:undecipunctata:howardi*
WCR western corn rootworm *Coleoptera:diabortica:virgifera:virgifera*
CPB colorado potato beetle *Coleoptera:leptinotarsa:decemlineata*
TBW tobacco budworm *Lepidoptera:noctuidea:heliothis:virescens*
THW tobacco hornworm *Lepidoptera:sphingidea:manuca:sexta*
Apical refers to those regions of cells those are exposed to the lumen of the midgut. Basal lamina refers to those regions extending of the midgut from the basal membrane of midgut lining cells to the basement membrane enclosing midgut.

Monoclonal antibodies were characterized for cross-reactivity with digestive tracts of other organisms including mammals. The selectivity and range of a given preferred antibody is determined by testing it against panels of (1) midgut cells from Coleoptera and Lepidoptera and (2) rat illeum cells. Twelve of fourteen monoclonal antibodies were found in general to be cross-reactive between different species of Diabrotica larval midgut and localized to similar regions (Table 1). Eight of fourteen monoclonal antibodies cross-reacted with Coleoptera relative of a different genus. Four monoclonal antibodies showed a distinct alteration in two localization pattern from Diabrotica midgut. Two monoclonal antibodies bound to the same midgut regions of different families of Lepidoptera. In mammalian tissue, two monoclonal antibodies were able to bind to rat illeum.

Isotyping Monoclonal Antibodies

Isotyping (antibody heavy and light chain types) were determined using a kit (Southern Biotechnology Associates, Birmingham, Ala.). Polystyrene plates were coated with goat anti-mouse antibodies (H+L) (Kirkegard and Perry Labs, Gaitherburg, Md.) diluted in 0.1M sodium carbonate, pH 9.6 at 10 g/ml and residual binding sites blocked with 1% BSA in PBS. Samples were incubated on these for about 10 min at 37° C., washed 3 times with 0.025% Tween 20 and probed with specific heavy and light chain goat antibodies conjugated to alkaline phosphatase for about 10° at 37° C. After washing, presence of colored product generated by alkaline phosphatase hydrolysis of p-nitrophenyl phosphate. Monoclonal antibodies to date have been largely IgG1 isotype with IgG2A, IgG2B and IgM isotypes in respective decreasing numbers.

Although the invention has been described in considerable detail, with reference to certain preferred embodiments thereof, it will be understood that variations and modifications can be affected within the spirit and scope of the invention as described above and as defined in the appended claims.

What is claimed is:

1. A monoclonal antibody which specifically binds to apical midgut intestinal membrane tissue of at least one insect species in the Order Lepidoptera and Coleoptera, wherein said antibody is selected from the group consisting of M2U85, produced by the hybridoma M2U85, M2U96, produced by the hybridoma M2U96, M2U100, produced by the hybridoma M2U100, and M2U110, produced by the hybridoma M2U110.

2. The antibody of claim 1 wherein the antibody is M2U85 and said antibody is produced by the hybridoma M2U85.

3. The antibody of claim 1 wherein the antibody is M2U96 and said antibody is produced by the hybridoma M2U96.

4. The antibody of claim 1 wherein the antibody is M2U100 and said antibody is produced by the hybridoma M2U100.

5. The antibody of claim 1 wherein the antibody is M2U110 and said antibody is produced by the hybridoma M2U110.

6. A hybridoma which produces a monoclonal antibody, said monoclonal antibody specifically binding to apical midgut intestinal membrane tissue of at least one insect species in the Order Lepidoptera and Coleoptera, wherein the hybridoma is selected from the group consisting of M2U85, M2U96, M2U100, and M2U110.

7. The hybridoma of claim 6 wherein the hybridoma is M2U85.

8. The hybridoma of claim 6 wherein the hybridoma is M2U96.

9. The hybridoma of claim 6 wherein the hybridoma is M2U100.

10. The hybridoma of claim 6 wherein the hybridoma is M2U110.

* * * * *